(12) United States Patent
Kataoka et al.

(10) Patent No.: US 8,455,209 B2
(45) Date of Patent: *Jun. 4, 2013

(54) REAGENT AND REAGENT KIT FOR ANALYSIS OF IMMATURE LEUKOCYTE

(75) Inventors: Yukiko Kataoka, Kobe (JP); Tomohiro Tsuji, Kobe (JP); Shinichiro Oguni, Kobe (JP); Ayumu Yoshida, Kobe (JP); Masaki Abe, Hamburg (DE)

(73) Assignee: Sysmex Corporation, Hyogo (JP)

( * ) Notice: Subject to any disclaimer, the term of this patent is extended or adjusted under 35 U.S.C. 154(b) by 632 days.

This patent is subject to a terminal disclaimer.

(21) Appl. No.: 12/666,774

(22) PCT Filed: Jun. 25, 2008

(86) PCT No.: PCT/JP2008/061572
§ 371 (c)(1),
(2), (4) Date: Dec. 24, 2009

(87) PCT Pub. No.: WO2009/001868
PCT Pub. Date: Dec. 31, 2008

(65) Prior Publication Data
US 2010/0184061 A1    Jul. 22, 2010

(30) Foreign Application Priority Data

Jun. 25, 2007 (JP) .............................. 2007-166609
Mar. 27, 2008 (JP) .............................. 2008-084137

(51) Int. Cl.
*G01N 33/00* (2006.01)

(52) U.S. Cl.
USPC .............. 435/7.24; 435/6.1; 435/7.21; 436/9; 436/10; 436/17; 436/63; 436/164; 436/175

(58) Field of Classification Search
USPC ................. 435/6.1, 7.21, 7.24; 436/9, 10, 17, 436/63, 164, 166, 175
See application file for complete search history.

(56) References Cited

U.S. PATENT DOCUMENTS

| | | | |
|---|---|---|---|
| 5,389,549 A | 2/1995 | Hamaguchi et al. | |
| 5,413,938 A | 5/1995 | Tsujino et al. | |
| 5,958,776 A | 9/1999 | Sakata et al. | |
| 6,664,110 B1 | 12/2003 | Tsuji et al. | |
| 6,869,798 B2 * | 3/2005 | Crews et al. | 436/10 |
| 7,625,757 B2 * | 12/2009 | Tsuji et al. | 436/10 |
| 2002/0086344 A1 | 7/2002 | Tsuji et al. | |
| 2003/0219850 A1 | 11/2003 | Tsuji et al. | |
| 2005/0202400 A1 | 9/2005 | Tsuji et al. | |

FOREIGN PATENT DOCUMENTS

| | | |
|---|---|---|
| EP | 444240 A1 * | 9/1991 |
| EP | 0525398 A2 | 2/1993 |
| EP | 1004880 A2 | 5/2000 |
| JP | 03-252556 A | 11/1991 |
| JP | 05-099919 A | 4/1993 |
| JP | 06-273413 A | 9/1994 |
| JP | 10-206423 A | 8/1998 |
| JP | 2000-162209 A | 6/2000 |
| JP | 2002-207036 A | 7/2002 |
| JP | 2002-223791 A | 8/2002 |
| JP | 2003-329668 A | 11/2003 |
| JP | 2006-091024 A | 4/2006 |
| JP | 2006-208401 A | 8/2006 |
| WO | 01/86264 A1 | 11/2001 |
| WO | 2004/001408 A1 | 12/2003 |

OTHER PUBLICATIONS

Zhou et al. Environmental Pollution (2011) 159: 1198-1204.*

* cited by examiner

*Primary Examiner* — Susan Hanley
(74) *Attorney, Agent, or Firm* — Sughrue Mion, PLLC (57) ABSTRACT

The present invention provides a reagent for analysis of immature leukocytes comprising:
  a surfactant which can damage cell membranes of erythrocytes and mature leukocytes,
  a solubilizing agent which can shrink the damaged blood cells and
  a dye for staining nucleic acid,
  wherein the reagent has an osmotic pressure of not lower than 10 mOsm/kg and lower than 150 mOsm/kg.

9 Claims, 8 Drawing Sheets

REAGENT AND REAGENT KIT FOR ANALYSIS OF IMMATURE LEUKOCYTE

CROSS-REFERENCE TO RELATED APPLICATIONS

The present application claims the priorities of Japanese Patent Application Nos. 2007-166609 and 2008-81437 filed on Jun. 25, 2007 and Mar. 27, 2008, respectively, and the entire contents thereof are incorporated herein by reference.

TECHNICAL FIELD

The present invention relates to a reagent and reagent kit for classifying and counting leukocytes in a biological sample.

BACKGROUND ART

Blood cells are produced in bone marrow, differentiated from immature cells to mature cells and migrated into peripheral blood. In healthy subject, immature leukocytes do not appear in peripheral blood. However, in some cases, immature leukocytes appear in peripheral blood of patients suffering from leukemia, cancer metastasis to the bone marrow, multiple myeloma, severe infection or the like. Therefore, it is very important to classify and measure mature and immature leukocytes in biological samples in order to diagnose these diseases.

A reagent disclosed in Japanese Unexamined Patent Publication No. Hei 10 (1998)-206423 is known as a reagent for measuring immature leukocytes. This reagent is mixed with a biological sample to form a measurement sample, the obtained measurement sample is introduced into a flow cytometer and mature and immature leukocytes in the sample are classified and respectively counted based on optical information obtained by applying light having a specific wavelength. Further, immature leukocytes can be further classified into myeloblasts, immature granulocytes and the like and they can be measured respectively.

DISCLOSURE OF THE INVENTION

Problems that the Invention is to Solve

In blood cell analysis using the conventional reagent, when blood cells are to be measured with a flow cytometer, for example, the signal region of the debris of lysed erythrocytes (erythrocyte ghosts) and the signal region of myeloblasts partially overlap, in some cases. In the analyses using such reagent, even when a blood sample containing no myeloblast is analyzed, the signal of the debris of erythrocytes is incorrectly recognized as the signal of myeloblasts so that the precise analysis result of blood cells could not be obtained. For example, peripheral blood from patients suffering from the specific diseases such as multiple myeloma, bile duct cancer, peritonitis, diabetes, gromerular nephritis, pleurisy or the like does not contain myeloblasts. However, when blood cells are analyzed in peripheral blood taken from such patients using the conventional reagent, there have been some cases in which a signal is detected in the region where myeloblasts are detected on the scattergram. The reason for this is considered to be that erythrocytes in the sample from such specific patients are not lysed properly, different from erythrocytes in the sample from healthy subject or patients with diseases other than those described above. There is a possibility of false diagnoses and treatments if the amount of myeloblasts detected in peripheral blood is higher than their actual amount. As used herein, the term "erythrocyte ghost" means erythrocytes which lost their hemoglobin as a result of the reaction of a blood sample and a regent for blood analysis, but did not shrink sufficiently.

Therefore, the purpose of the present invention is to provide a reagent which makes it possible to classify and count immature leukocytes more precisely even when blood samples from the patients with such specific diseases as described above are analyzed.

Means for Solving the Problems

The present inventors have made intensive studies to solve the above-described problems and found that the above problems can be solved by decreasing osmotic pressure of the reagent for analysis of immature leukocytes to the level lower than that has been used conventionally.

It has been considered that the conventional reagent for analysis of immature leukocytes is suitable to have the osmotic pressure similar to that of immature leukocytes and mature leukocytes in order to prevent the lysis of these blood cells at the time of the measurement.

However, it is found now that the accuracy of the analysis of biological samples from patients suffering from the specific diseases such as multiple myeloma, bile duct cancer, peritonitis, diabetes, gromerular nephritis, pleurisy or the like is improved when an analysis reagent having surprisingly low osmotic pressure compared to the common technical knowledge is used. For example, by using the analysis reagent having low osmotic pressure, myeloblasts and lysed erythrocytes could be discriminated more clearly. Moreover, surprisingly, it is now found that the analysis reagent of the present invention makes it possible to distinguish immature leukocytes from mature leukocytes as clear as the conventional reagent having high osmotic pressure does, even for biological samples from patients suffering from diseases other than the above specific diseases. For example, it is found that erythrocyte ghosts can be prevented to appear by using the analysis reagent of the present invention.

Depending on specimens, there is some cases in which the signal of myeloblasts and the signal of basophils overlap even when a reagent having low osmotic pressure is used. Due to this, there was a possibility that myeloblasts are identified in peripheral blood of healthy subject, although myeloblasts do not exist therein to lead to a false result. This further problem that the signals of myeloblasts and basophils overlap could be solved by decreasing the concentrations of a surfactant and a solubilizing agent in the reagent for analysis of immature leukocytes to the level lower than that has been considered conventionally. Accordingly, it becomes possible to more clearly distinguish basophils from myeloblasts even in blood samples containing high amount of basophils by using the reagent of the present invention. Further, decrease of the concentrations of a surfactant and a solubilizing agent allows classification of mature leukocytes into at least three species under low osmotic pressure condition.

One aspect of the present invention is a reagent for analysis of immature leukocytes comprising:

a surfactant which can damage cell membranes of erythrocytes and mature leukocytes, a solubilizing agent which can shrink the damaged blood cells and a dye for staining nucleic acid, wherein the reagent has an osmotic pressure of not lower than 10 mOsm/kg and lower than 150 mOsm/kg.

Another aspect of the present invention is a reagent kit for analysis of immature leukocytes comprising:

a first reagent which comprises a surfactant that can damage cell membranes of erythrocytes and mature leukocytes and a solubilizing agent that can shrink the damaged blood cells and which has an osmotic pressure of not lower than 10 mOsm/kg and lower than 150 mOsm/kg, and a second reagent which comprises a dye for staining nucleic acid.

Further aspect of the present invention is a method for classifying immature leukocytes comprising the steps of:

mixing a biological sample possibly containing immature leukocytes with a reagent for analysis of immature leukocytes comprising a surfactant which can damage cell membranes of erythrocytes and mature leukocytes, a solubilizing agent which can shrink the damaged blood cells and a dye for staining nucleic acid, and having an osmotic pressure of not lower than 10 mOsm/kg and lower than 150 mOsm/kg, to stain nucleic acid of mature leukocytes, and measuring at least one scattered light and at least one fluorescence of the immature leukocytes treated in the previous step to classify immature leukocytes based on differences in intensities of the scattered light and the fluorescence.

Effect of the Invention

The reagent and reagent kit for analysis of immature leukocytes of the present invention allow more precise classification and count of immature leukocytes and mature leukocytes compared to the conventional reagent, even when biological samples from patients suffering from the specific diseases such as multiple myeloma, bile duct cancer, peritonitis, diabetes, gromerular nephritis, pleurisy or the like are analyzed.

BRIEF DESCRIPTION OF DRAWINGS

FIGS. 2 (1), 2 (2), 2 (3), and 2 (4) represent scattergrams obtained in Example 1.

FIGS. 3 (1), 3 (2), 3 (3), and 3 (4) represent scattergrams obtained in Example 2.

FIGS. 4 (1), 4 (2) 4 (3), and 4 (4) represent scattergrams obtained in Example 3.

FIGS. 5 (A) and 5 (B) represent scattergrams obtained in Example 4.

FIGS. 6 (A) and 6 (B) represent scattergrams obtained in Example 5.

FIGS. 7 (A) and 7 (B) represent scattergrams obtained in Example 6.

FIGS. 8 (A) and 8 (B) represent scattergrams obtained in Example 7.

FIGS. 9 (A) and 9(B) represent scattergrams obtained in Example 8.

FIGS. 10 (A) and 10 (B) represent scattergrams obtained in Example 9.

FIGS. 11 (A) and 11 (B) represent scattergrams obtained in Example 10.

| DESCRIPTION OF THE REFERENCE NUMERALS | |
|---|---|
| 6 | Nozzle |
| 21 | Light source |
| 22 | Collimator lens |
| 23 | Flow cell |

| DESCRIPTION OF THE REFERENCE NUMERALS | |
|---|---|
| 24 | Condensing lens |
| 25 | Pin hole plate |
| 26 | Forward scattered light detector |
| 27 | Condensing lens |
| 28 | Dichroic mirror |
| 28' | Filter |
| 29 | Side scattered light detector |
| 30 | Pin hole plate |
| 31 | Side fluorescence detector |
| 32, 33 and 34 | Amplifiers |
| 35 | Analyzing part |

BEST MODE FOR CARRYING OUT THE INVENTION

The reagent for analysis of immature leukocytes of the present embodiment (hereinafter referred to as "the reagent") makes it possible to classify leukocytes contained in a biological sample into mature and immature leukocytes and to count them respectively. It also makes it possible to classify the mature leukocytes into at least three species such as lymphocytes, monocytes, granulocytes, basophils and the like and to count them respectively. Further, the present reagent makes it possible to further classify immature leukocytes into immature granulocytes and myeloblasts and to accurately count them respectively.

The term "immature leukocytes" as used herein refers to immature leukocytes which exist usually in bone marrow and do not occur in peripheral blood of healthy subject. Immature leukocytes include, for example, myeloblasts, promyelocytes, myelocytes, metamyelocytes, and the like. In some cases, promyelocytes, myelocytes and metamyelocytes are collectively called as "immature granulocytes". Myeloblasts include leukocytic hematopoietic precursor cells such as myeloid series stem cells (CFU-GEMN), neutrophil-macrophage colony-forming cells (CFU-GM), eosinophil colony-forming cells (CFU-EOS) and the like.

The biological sample to be analyzed with the reagent of the present embodiment is not limited as long as it comprises leukocytes and includes, for example, blood, urea, bone marrow aspirate, a sample taken in apheresis and the like.

The reagent of the present embodiment comprises the surfactant which can damage cell membranes of erythrocytes and mature leukocytes, the solubilizing agent which can shrink the damaged blood cells and the dye for staining nucleic acid and has an osmotic pressure of not lower than 10 mOsm/kg and lower than 150 mOsm/kg.

By mixing the biological sample and the reagent, cell membranes of blood cells contained in the sample are damaged by the action of the surfactant and the solubilizing agent. The surfactant tends to damage cell membranes of erythrocytes and mature leukocytes, while cell membranes of immature leukocytes are resistant to be damaged. The damaged blood cells such as erythrocytes and mature leukocytes shrink by the action of the solubilizing agent. On the other hand, because cell membranes of immature leukocytes are difficult to be damaged, these cells are less shrunk by the solubilizing agent than erythrocytes and mature leukocytes.

Among the damaged blood cells, the nuclei of leukocytes tend to be stained intensely by the action of the dye for staining nucleic acid. However, the undamaged immature leukocytes are difficult to be stained. In addition, because erythrocytes do not have nuclei, they are difficult to be stained by the above dye for staining nucleic acid. As a consequence, immature leukocytes, mature leukocytes and erythrocytes can be respectively discriminated.

The osmotic pressure of the reagent of the present embodiment is not lower than 10 mOsm/kg and lower than 150 mOsm/kg, preferably 10 to 100 mOsm/kg, and more preferably 10 to 60 mOsm/kg. Such osmotic pressure can be obtained by mixing the components described hereinafter in the amount described hereinafter, or by suitably adjusting the concentration of a buffering agent. However, it is also possible to adjust the pressure by adding saccharides, amino acids, sodium chloride and the like, if desired.

The saccharides may mention monosaccharides such as glucose, fructose and the like; polysaccharides such as arabinose and the like; and sugar alcohols such as xylitol, sorbitol, mannitol, ribitol and the like, without any limitation thereto.

When xylitol is used, for example, it may be used in an amount of 0 to 10 g/L, more preferably 4 to 8 g/L in the reagent.

The amino acids may include valine, proline, glycine, alanine and the like. It is preferred to use either or both of glycine and alanine.

When glycine is used, for example, it may be used in an amount of 0 to 10 g/L, more preferably 2 to 6 g/L in the reagent.

The surfactant which can damage cell membranes of erythrocytes and mature leukocytes is preferably an nonionic surfactant and is more preferably a polyoxyethylene nonionic surfactant. The polyoxyethylene nonionic surfactant is more preferably the one having the following formula (I):

$$R^1\text{-}R^2\text{—}(CH_2CH_2O)n\text{—}H \qquad (I)$$

(wherein $R^1$ represents a $C_{9\text{-}25}$ alkyl, alkenyl or alkynyl group; $R^2$ represents —O—, —COO— or and n is an integer of 10 to 40).

The surfactant represented by the above formula (I) may include polyoxyethylene(15)oleyl ether, polyoxyethylene(20)oleyl ether, polyoxyethylene(20)stearyl ether, polyoxyethylene(15)cetyl ether, polyoxyethylene(20)cetyl ether and the like. The surfactant can be one or more species.

The concentration of the surfactant in the reagent can be appropriately selected according to the type of the surfactant. When the surfactant is the polyoxyethylene oleyl ether, the concentration thereof in the reagent is preferably 500 to 15,000 ppm, more preferably 750 to 10,000 ppm, and further preferably 1,000 to 2,500 ppm.

In more preferred embodiment of the present invention, the concentration of the surfactant is set to a relatively low range such as 1,000 to 10,000 ppm, for example. In such concentration range, the damage to the cell membranes of one of the mature leukocytes, basophils, is suppressed than the case when the reagent having relatively high concentration of the surfactant is used, so that it can be prevented that the basophils are damaged and cellular components of the basophils are released to the outside of the cells. Accordingly, basophils are easy to be stained by the action of the dye for staining nucleic acid as similar to other mature leukocytes. On the other hand, cell membranes of one of immature leukocytes, myeloblasts, are not damaged as above so that they are difficult to be stained. As a consequence, basophils and myeloblasts are more efficiently discriminated.

When multiple surfactants are used, the mixing ratio of these surfactants can be appropriately selected according to a hydroxyl value of the surfactants. For example, when polyoxyethylene(15)oleyl ether having the hydroxyl value of 64.8 and polyoxyethylene(20)oleyl ether having the hydroxyl value of 52.4 are used, the mixing ratio is preferably 1:9.

The above solubilizing agent may include, for example, sarcosine derivatives, cholic acid derivatives, methylglucanamides and the like. One or more selected among them can be used.

Sarcosine derivatives include the sarcosine derivatives having the following structural formula and salts thereof. Specifically, sodium N-lauroylsarcosinate, sodium lauroyl methyl β-alanine, lauroylsarcosine and the like are mentioned. Colic acid derivatives include the colic acid derivatives having the following structural formula and salts thereof. Specifically, CHAPS (3-[(3-cholamidopropyl)dimethylammonio]-1-propanesulfonate), CHAPSO ([(3-cholamidopropyl)dimethylammonio]-2-hydroxy-1-propanesulfonate) and the like are mentioned. Methylglucanamides include MEGA8 (octanoyl-N-methylglucamide), MEGA9 (nonanoyl-N-methylglucamide), MEGA10 (decanoyl-N-methylglucamide) and the like.

Sarcosine derivatives have the following structural formula:

wherein $R_1$ is a $C_{10\text{-}22}$ alkyl group; and n is 1 to 5.

Colic acid derivatives have the following structural formula:

wherein $R_1$ is a hydrogen atom or a hydroxy group.

Methylglucanamides have the following structural formula:

wherein n is 5 to 7.

The concentration of the solubilizing agent in the reagent can appropriately be selected according to the type of the solubilizing agent used. When the sarcosine derivative is used as the solubilizing agent, the concentration of the solubilizing agent in the reagent is preferably 50 to 3,000 ppm, more preferably 100 to 400 ppm. When the colic acid derivative is used, it is preferably 50 to 10,000 ppm, more preferably 50 to 1,300 ppm. When the methylglucanamide is used, it is preferably 500 to 8,000 ppm, more preferably 500 to 1,100 ppm.

Further, n-octyl β-glucoside, sucrose monocaprate, N-formylmethylleucylalanine and the like can be used as the solubilizing agent. When these are used, the concentration thereof in the reagent is preferably 5 to 50,000 ppm, more preferably 5 to 6,600 ppm. One or more solubilizing agents may be used alone or in combination.

In more preferred embodiment of the present invention, due to relatively low concentration of the solubilizing agent, the damage to the cell membranes of one of mature leukocytes, basophils, is suppressed than the case when the reagent having relatively high concentration of the solubilizing agent is used, so that it can be prevented that the basophils are damaged and cellular components of the basophils are released to the outside of the cells. Accordingly, basophils are easy to be stained by the action of the dye for staining nucleic acid as similar to other mature leukocytes. On the other hand, cell membranes of one of immature leukocytes, myeloblasts, are not damaged as above so that they are difficult to be stained. As a consequence, basophils and myeloblasts are more efficiently discriminated.

The above dye for staining nucleic acid is not limited as long as it can stain nucleic acid, and is preferably a fluorescent dye. By using such a dye, erythrocytes having no nucleic acid are hardly stained, while leukocytes having nucleic acid are stained intensely. Based on the difference in the intensity of the staining, erythrocytes and leukocytes can be discriminated. In addition, mature leukocytes whose cell membrane is damaged such that the dye can permeate are stained intensely by the dye, while mostly undamaged immature leukocytes are hard to be stained. Based on the difference in the intensity of the staining, mature leukocytes and immature leukocytes among leukocytes can be discriminated.

The dye for staining nucleic acid are appropriately selected according to the light to be applied in an analysis. For example, the dyes having the following structural formulae are preferably used.

(1) A dye having the following formula (II):

(II)

wherein $R_1$ and $R_2$ are a lower alkyl group; n is 1 or 2; $X^-$ is an anion; and Z is a sulfur atom, an oxygen atom, or a carbon atom which is substituted by a lower alkyl group.

The lower alkyl group with regard to $R_1$ and $R_2$ of the above formula (II) refers to a $C_{1-6}$ straight or branched alkyl group. It includes, for example, methyl, ethyl, propyl, butyl, isobutyl, sec-butyl, tert-butyl, pentyl and hexyl groups, among which methyl group is preferred.

The lower alkyl group with regard to Z includes the same groups as the above. Z is preferably a sulfur atom.

The anion with regard to $X^-$ includes halogen ions (fluoride, chloride, bromide or iodide ion), boron halide ions ($BF_4^-$, $BCl_4^-$, $BBr_4^-$, etc.), phosphorus compound ions, halogeno-oxygen acid ions, fluorosulfuric acid ions, methyl sulfate ions, and tetraphenyl boron compound ions which have a halogen or halogeno-alkyl group as a substituent on the aromatic rings. Among them, iodide ion is preferred.

The following dye is suitable as the dye for staining nucleic acid having the above formula (II).

Dye A:

(2) A dye having the following formula (III):

(III)

wherein $R_1$ and $R_2$ are a lower alkyl group; n is 1 or 2; and $X^-$ is an anion.

The same can be mentioned for the lower alkyl group of $R_1$ and $R_2$ and the anion of $X^-$ in the above formula (III) as those described for the above formula (II).

The following dye is suitable as the dye for staining nucleic acid having the above formula (III).

Dye B:

(3) A dye having the following formula (IV):

(IV)

wherein $R_1$ is a hydrogen atom or a lower alkyl group; $R_2$ and $R_3$ are a hydrogen atom, a lower alkyl group or a lower alkoxy group; $R_4$ is a hydrogen atom, an acyl group or a lower alkyl group; $R_5$ is a hydrogen atom or an optionally substituted lower alkyl group; Z is a sulfur atom, an oxygen atom, or a carbon atom which is substituted by a lower alkyl group; n is 1 or 2; and $X^-$ is an anion.

The same can be mentioned for the lower alkyl group of $R_1$ in the above formula (IV) as those described for the above formula (II).

The same as above can be mentioned for the lower alkyl group of $R_2$ and $R_3$. The lower alkoxy group means a $C_{1-6}$ alkoxy group and includes methoxy, ethoxy and propoxy groups, among which methoxy and ethoxy groups are preferred. $R_2$ and $R_3$ are preferably a hydrogen atom.

In the above formula (IV), the acyl group of $R_4$ is preferably an acyl group derived from an aliphatic carboxylic acid and includes, for example, acetyl, propionyl and the like, among which an acetyl group is preferred. The above lower alkyl groups are mentioned.

The same can be mentioned for the lower alkyl group of $R_5$. The optionally substituted lower alkyl group means a lower alkyl group which may be substituted by one to three hydroxy groups, halogen atoms (fluorine, chlorine, bromine or iodine) and the like and is preferably a methyl or ethyl group substituted by one hydroxy group.

The same as above can be mentioned for the lower alkyl group of Z. Z is preferably a sulfur atom.

The anion of $X^-$ is preferably a bromide ion or $BF_4^-$.

The following dyes are suitable as the dye for staining nucleic acid having the above formula (IV).

Dye C:

(4) A dye having the following formula (V):

wherein $X_1$ and $X_2$ are independently Cl or I.

(5) A dye having the following formula (VI) (NK-3975):

(6) A dye having the following formula (VII) (NK-1570):

(7) A dye having the following formula (VIII) (NK-1049):

(8) A dye having the following formula (IX) (NK-98):

(9) A dye having the following formula (X) (NK-141):

(10) Propidium iodide or ethidium bromide.

(11) Ethidium-acridine heterodimer, ethidium diazide, ethidium homodimer-1, ethidium homodimer-2, ethidium monoazide, trimethylene bis[[3-[[4-[[(3-methylbenzothiazol-3-ium)-2-yl]methylene]-1,4-dihydroquinoline]-1-yl]propyl]dimethylaminium]tetraiodide (TOTO-1), 4-[(3-methylbenzothiazol-2(3H)-ylidene)methyl]-1-[3-(trimethylamino)propyl]quinolinium diiodide (TO-PRO-1), N,N,N',N'-tetramethyl-N,N'-bis[3-[4-[3-[(3-methylbenzothiazol-3-ium)-2-yl]-2-propenylidene]-1,4-dihydroquinoline-1-yl]propyl]1,3-propanediaminium tetraiodide (TOTO- 3), or 2-[3-[[1-[3-(trimethylamino) propyl]1,4-dihydroquinoline]-4-ylidene]-1-pr openyl]3-methylbenzothiazol-3-ium diiodide (TO-PRO-3).

The concentration of the above dye is preferably 0.01 to 500 ppm, and more preferably 0.1 to 200 ppm in the reagent. The above dye may be used alone or two or more dyes may be combined.

The pH of the reagent according to the present embodiment is preferably 5.0 to 9.0, more preferably 6.5 to 7.5, and still more preferably 6.8 to 7.3. The pH of the reagent can be adjusted with a buffering agent. The buffering agent used can be, for example, Good buffer such as HEPES, MOPS (3-morpholinopropanesulfonic acid), MOPSO (2-hydroxy-3-morpholinopropanesulfonic acid) or BES (2-[bis(2-hydroxyethyl)amino]ethanesulfonic acid), phosphate buffered saline and the like. A pH adjusting agent such as sodium hydroxide can also be used.

The reagent of the present embodiment can be obtained by dissolving the above surfactant, solubilizing agent, dye for staining nucleic acid and optional component(s) in an appropriate medium with the concentrations described above. The appropriate medium is not limited as long as it can dissolve the above components and includes water, alcohol, ethylene glycol, dimethylsulfoxide (DMSO), the mixture thereof and the like.

The above surfactant, solubilizing agent and dye for staining nucleic acid can be used as a single reagent to be mixed with a biological sample for analysis of immature leukocytes. Alternatively, a reagent kit containing a first reagent comprising the surfactant and solubilizing agent and a second reagent comprising the dye for staining nucleic acid can be used for analysis of immature leukocytes.

Therefore, the present invention also provides a reagent kit for analysis of immature leukocytes comprising a first reagent which comprises a surfactant that can damage cell membranes of erythrocytes and mature leukocytes and a solubilizing agent that can shrink the damaged blood cells and which has an osmotic pressure of not lower than 10 mOsm/kg and lower than 150 mOsm/kg, and a second reagent which comprises a dye for staining nucleic acid.

The concentrations of the surfactant and solubilizing agent in the above first reagent may be such that the concentrations thereof described above for the reagent for analysis of immature leukocytes can be obtained when the first reagent is mixed with the second reagent. The osmotic pressure of the first reagent can be adjusted to the desired range by dissolving the surfactant and solubilizing agent to the appropriate medium described above and appropriately adjusting the amount of the buffering agent, if desired. The above saccharides, amino acids and the like may be used for the adjustment.

The concentration of the dye for staining nucleic acid in the second reagent may be such that the concentration thereof described above for the reagent for analysis of immature leukocytes can be obtained when the second reagent is mixed with the first reagent. It is preferable that the second reagent is the one in which the dye for staining nucleic acid is dissolved in an organic solvent such as ethylene glycol because the storage stability of the dye can be improved.

The reagent and reagent kit can be used for the analysis of immature leukocytes by preparing a measurement sample by mixing the reagent(s) with a biological sample and subjecting the measurement sample to a flow cytometer. The mixing ratio (by volume) of the biological sample and the reagent or the sum of the first and second reagents in the reagent kit is preferably 1:10 to 1:1,000.

In the reagent kit, the mixing ratio (by volume) of the first and second reagents is preferably 1,000:1 to 10:1.

When the reagent kit is used, the order of addition for mixing the respective reagent in the reagent kit and the biological sample is not specifically limited. Preferably, the first reagent and the second reagent are mixed and then the biological sample is added thereto.

The condition for mixing the reagent or the reagents in the reagent kit and the biological sample can be appropriately selected according to the reagent(s). For example, the temperature and the reaction time can be selected from 20 to 40° C. and 3 to 30 seconds, respectively. When the reaction temperature is high, the reaction time can be shorter; when the reaction temperature is low, the reaction time can be longer.

When a flow cytometer is used for the analysis, light can be applied to the blood cells in the measurement sample flowing through a flow cell to obtain optical information such as scattered light, fluorescence and the like. The species and number of the blood cells can be measured based on the information.

Figure 1:
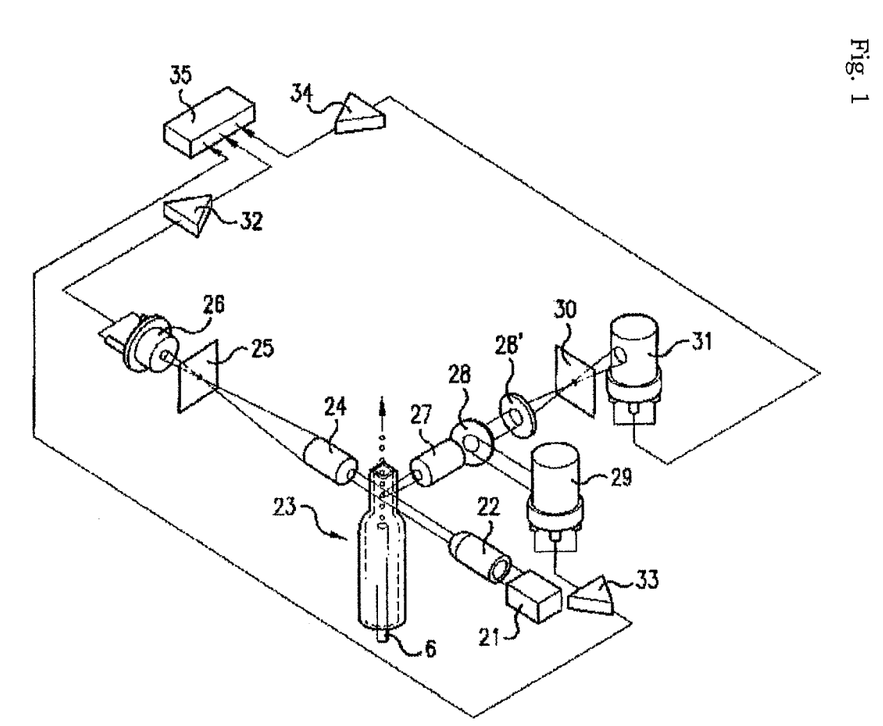
FIG. 1 is a schematic representation showing an example of a flow cytometer which can be used for analyses of immature leukocytes using the reagent or reagent kit of the present invention.
Figure 2:
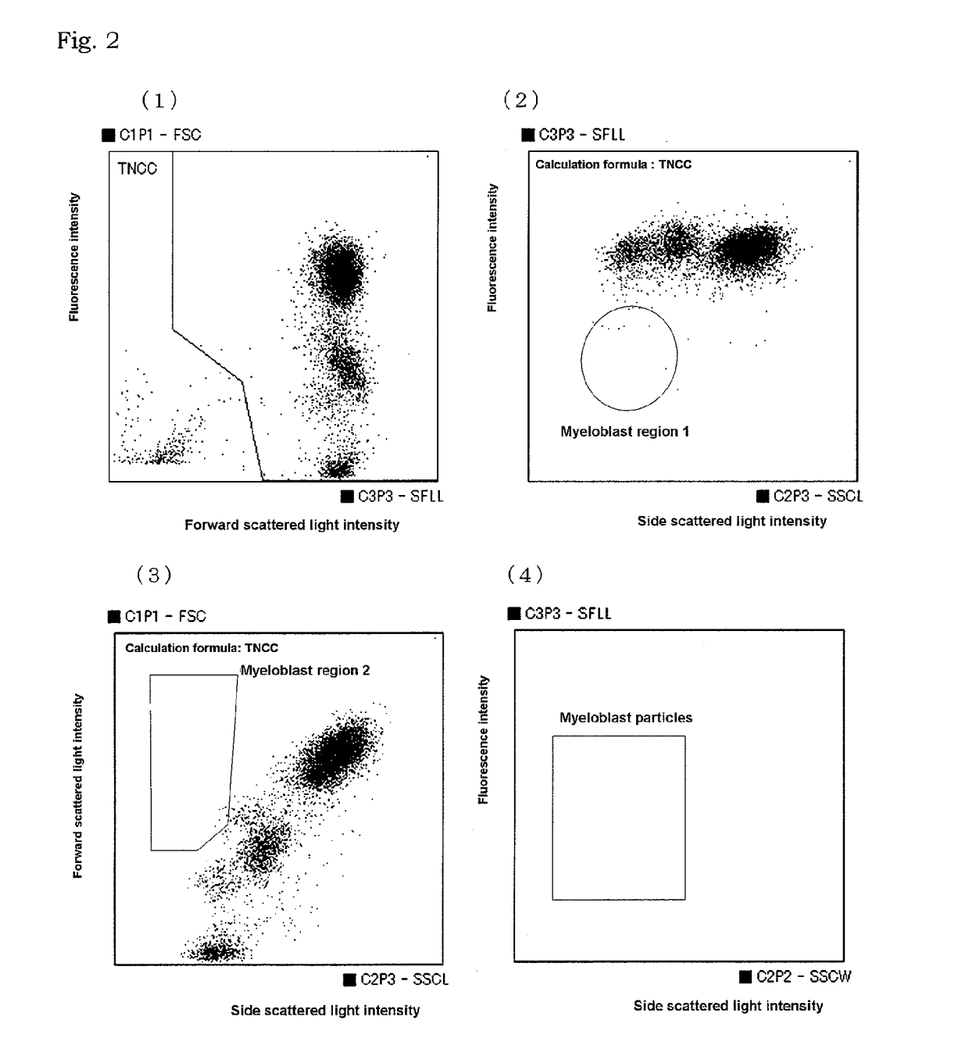
Figure 3:
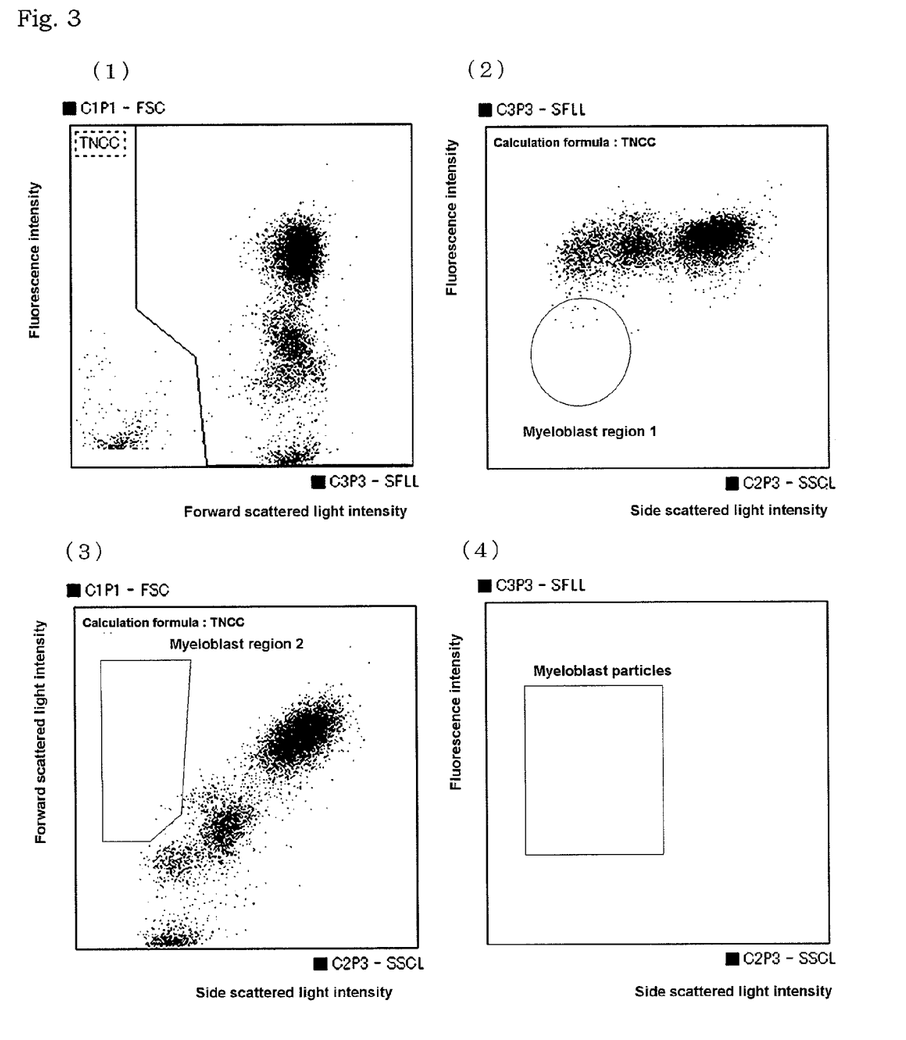
Figure 4:
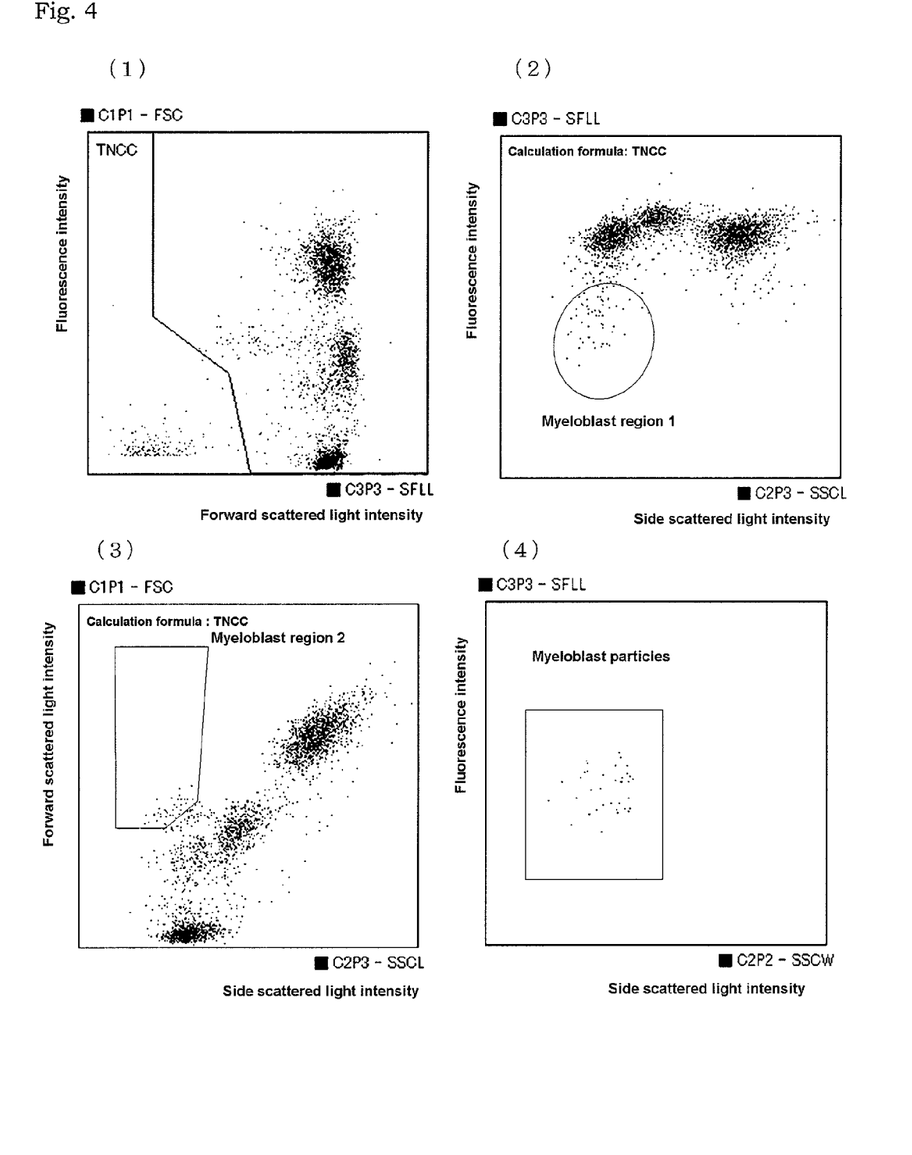
Figure 5:
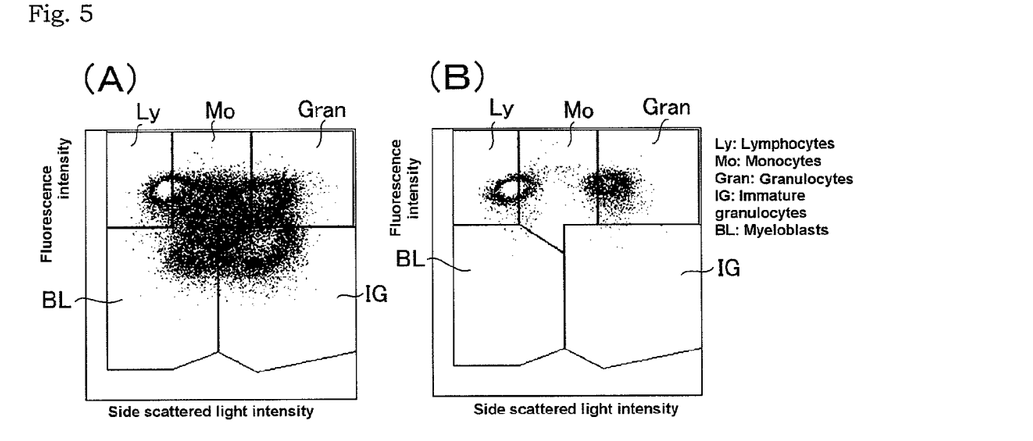
Figure 6:
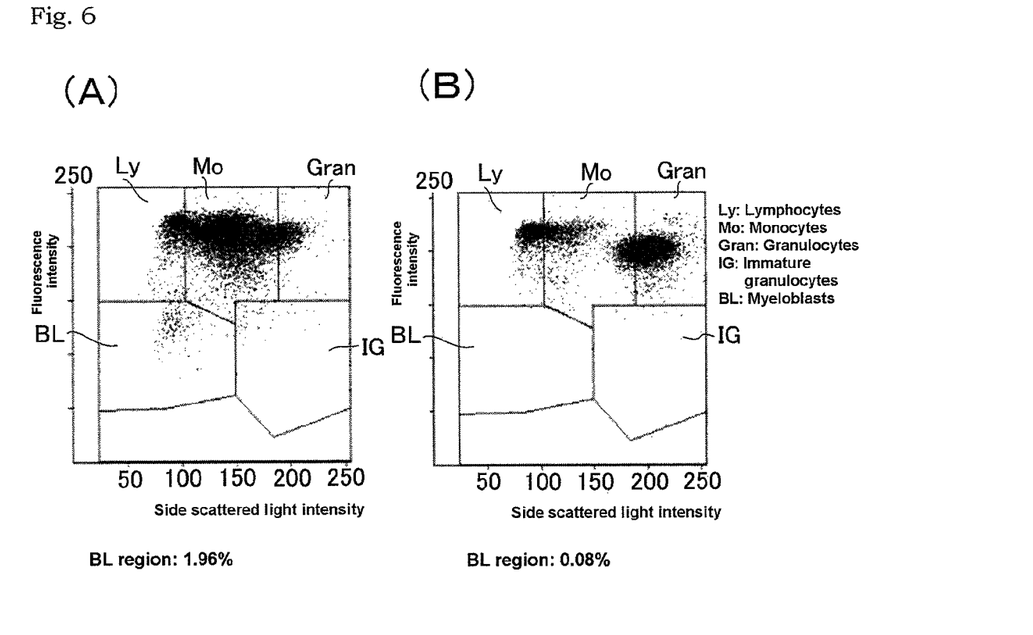
Figure 7:
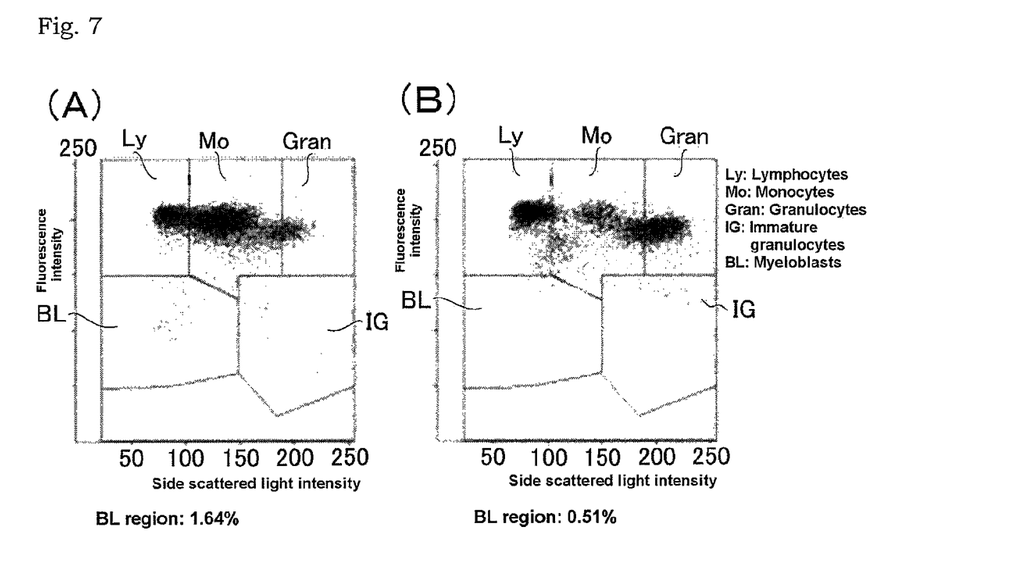
Figure 8:
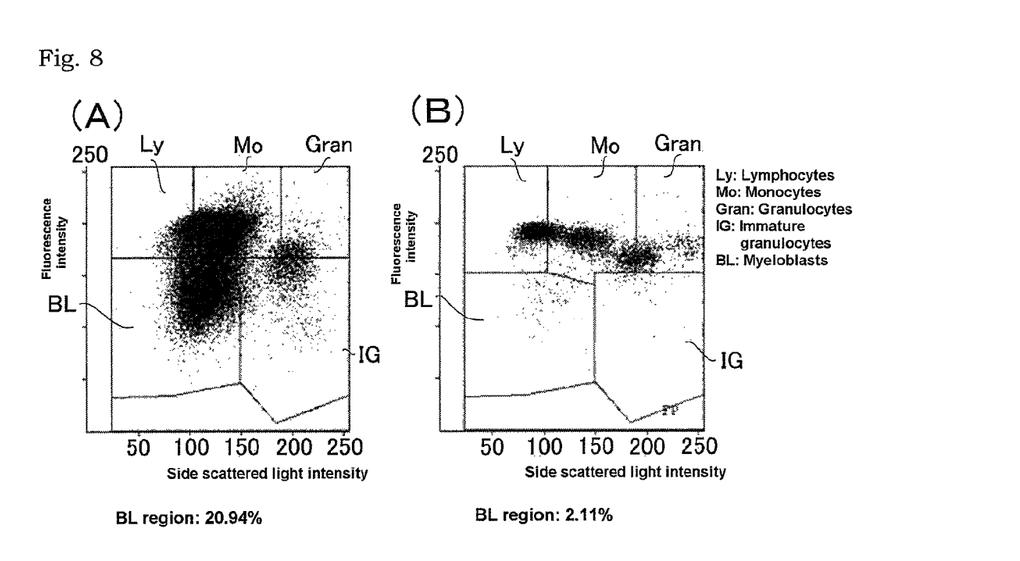
Figure 9:
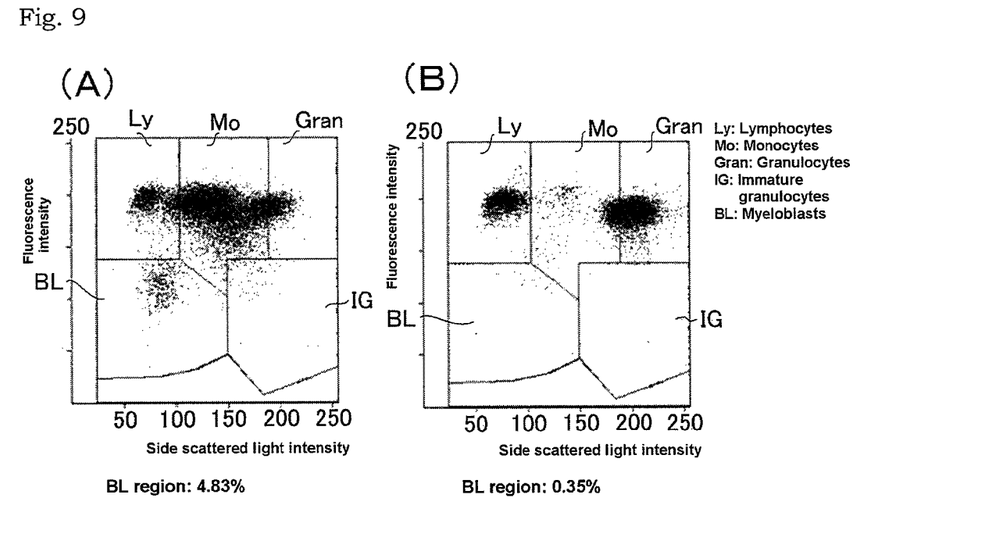
Figure 10:
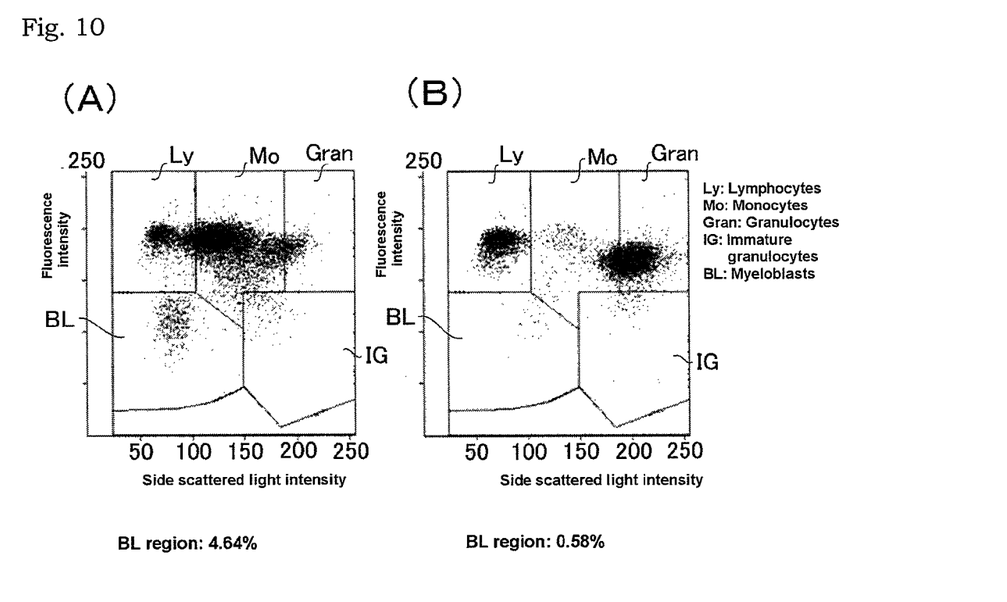
Figure 11:
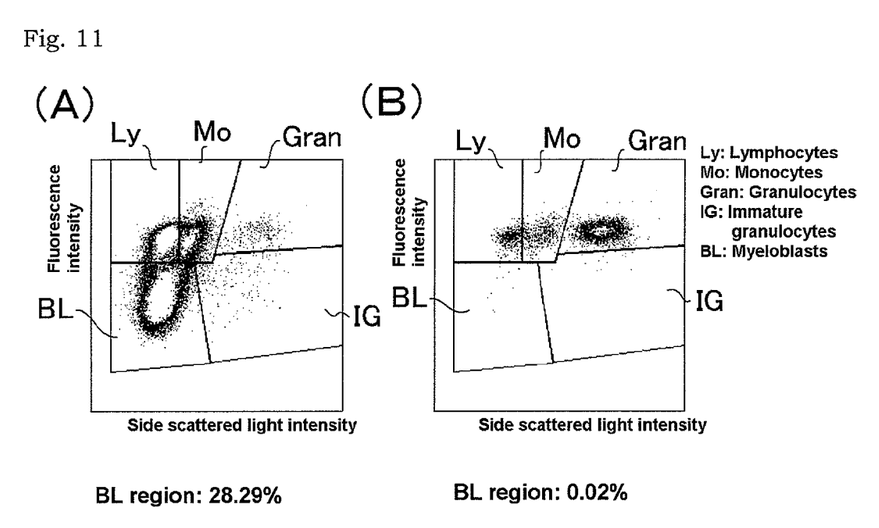

Specifically, the above analysis can be carried out by using the flow cytometer shown in FIG. 1. In the following, a measurement of myeloblasts is described as an example of the present embodiments.

A measurement sample discharged from a nozzle 6 flows through an orifice portion of a flow cell 23. Blood cells in the sample pass through the orifice portion in a line. Light emitted from a light source 21 is applied via a collimator lens 22 to blood cells flowing through the flow cell 23. Side scattered light, side fluorescence and forward scattered light are generated by applying light to the blood cells. The side scattered light is introduced into a side scattered light detector (photomultiplier tube) 29 through a condensing lens 27 and a dichroic mirror 28. The side fluorescence is introduced into a side fluorescence detector (photomultiplier tube) 31 through the condensing lens 27, the dichroic mirror 28, a filter 28' and a pin hole plate 30. The forward scattered light is introduced into a forward scattered light detector (photodiode) 26 through a condensing lens 24 and a pin hole plate 25.

The forward scattered light signal, side scattered light signal and side fluorescence signal generated from the forward scattered light detector 26, the side scattered light detector 29 and the side fluorescence detector 31, respectively, are amplified by amplifiers 32, 33, and 34, respectively, and introduced into an analyzing part 35.

The analyzing part 35 calculates the intensities of the forward scattered light, side scattered light and fluorescence respectively from the introduced forward scattered light signal, side scattered light signal and side fluorescence signal. The analyzing part 35 generates a first two-dimensional distribution map having two axes of the forward scattered light intensity and the fluorescence intensity and identifies a region where all leukocytes in the sample appear (total leukocyte region) on the two-dimensional distribution map. Further, the analyzing part generates a second two-dimensional distribution map having two axes of the side scattered light intensity and the fluorescence intensity of the cells appearing in the total leukocyte region. On this two-dimensional distribution map, a region where mature leukocytes appear (mature leukocyte region), a region where lymphocytes appear (lymphocyte region), a region where monocytes appear (monocyte region) and a region where granulocytes appear (granulocyte region) are established. Further, a region where myeloblasts appear (myeloblast region 1) and a region where immature granulocytes appear (immature granulocyte region) are identified.

Then, a third two-dimensional distribution map is generated having two axes of the side scattered light intensity and the forward scattered light intensity, and a region where myeloblasts appear (myeloblast region 2) on this two-dimensional distribution map is identified. The number of myeloblasts contained in the sample is calculated as the number of cells appearing in the myeloblast region 1 and the myeloblast region 2, and the number of immature granulocytes contained in the sample is calculated as the number of cells appearing in the immature granulocyte region. Incidentally, because myeloblasts have large size and have single nucleus, they generate strong forward scattered light intensity and weak side scattered light intensity. In addition, they generate weak fluorescence intensity because they are hardly stained, as described above. Because immature granulocytes have large size and their nuclei are segmented, they generate strong forward scattered light intensity and side scattered light intensity. In addition, they generate weak fluorescence intensity because they are hardly stained.

The present invention further provides a method for analyzing immature leukocytes comprising mixing the present reagent for analysis or the reagents in the reagent kit for analysis with a biological sample.

In the preferred embodiment of the method of the present invention, the concentration of the surfactant in the reagent for analysis or the mixed reagent of the first and second reagents in the reagent kit for analysis is preferably 500 to 15,000 ppm, more preferably 750 to 10,000 ppm and further preferably 1,000 to 2,500 ppm.

In another preferred embodiments of the method of the present invention, when the sarcosine derivative or the salt thereof is used as the solubilizing agent, the concentration of the solubilizing agent in the reagent or in the mixed reagent of the first and second reagents of the reagent kit is 100 to 400 ppm; when the colic acid derivative is used, it is 50 to 1,300 ppm; and when the methylglucanamide is used, it is 500 to 1,100 ppm.

According to these preferred embodiments, basophils and myeloblasts in the biological sample can be discriminated more clearly.

EXAMPLES

The present invention will be explained by the following examples in more detail. However, the present invention is not limited by the following examples.

Example 1

A first reagent and second reagent having the following composition were prepared.
<First Reagent>

| | |
|---|---|
| Polyoxyethylene(20)oleyl ether (Nikko Chemicals) | 2000 ppm |
| Sodium N-lauroylsarcosinate (commercial product) | 125 ppm |
| MOPSO (commercial product) | 10 mM |
| Purified water | 1 L |

The above components were mixed and pH was adjusted to 7.0 with NaOH. The osmotic pressure and electric conductivity of the first reagent were 20 mOsm/kg and 0.78 mS/cm, respectively.

<Second Reagent>

| | |
|---|---|
| Dye for staining nucleic acid | 50 ppm |
| Ethylene glycol | 1 L |

The dye was dissolved into ethylene glycol to prepare the second reagent. As the dye for staining nucleic acid, the dye C described above was used.

The first reagent (980 µl), 20 µL of the second reagent and 20 µL of a blood sample collected from a healthy donor (ratio of basophils being 2.1%, no myeloblast being contained) were mixed and reacted at 35° C. for 19 seconds to prepare a measurement sample. The obtained measurement sample was subjected to the flow cytometer shown in FIG. 1 and side scattered light intensity, forward scattered light intensity and fluorescence intensity were measured. The light source used was red semiconductor laser.

Based on the obtained forward scattered light intensity and fluorescence intensity, a first two-dimensional distribution map (scattergram) having two axes of the forward scattered light intensity and the fluorescence intensity was generated. According to this first two-dimensional distribution map, the total leukocyte region was identified. The number of the cells appearing in the identified total leukocyte region was calculated as the number of total leukocytes contained in the sample. FIG. 2 (1) shows the obtained scattergram. For the cells appearing in the identified total leukocyte region, a second two-dimensional distribution map (scattergram) having two axes of the side scattered light intensity and fluorescence intensity and a third two-dimensional distribution map (scattergram) having two axes of the side scattered light intensity and the forward scattered light intensity were generated. On the second and third two-dimensional distribution maps, the myeloblast regions 1 and 2 were established. FIGS. 2 (2) and (3) show the obtained scattergrams. The number of the cells appearing in the myeloblast regions 1 and 2 were calculated as the number of myeloblasts contained in the sample. FIG. 2 (4) shows the obtained scattergram.

As can be seen from FIGS. 2 (1) to (4), no signal is detected in the scattergram at a region where the potential signal of myeloblasts appears, because no myeloblast is contained in the blood sample from the healthy donor. No signal for lysed erythrocytes is appeared. Further, basophils do not appear in the myeloblast region because they are stained as intense as other mature leukocytes.

The ratio of myeloblasts to total leukocytes (ratio of myeloblasts=the number of myeloblasts/the number of total leukocytes×100) was calculated to be 0%. The visually confirmed ratio of myeloblasts was also 0%.

Example 2

A first reagent having the following composition was prepared.
<First Reagent>

| | |
|---|---|
| Polyoxyethylene(20)oleyl ether (Nikko Chemicals) | 1500 ppm |
| Sodium N-lauroylsarcosinate (commercial product) | 225 ppm |
| MOPSO (commercial product) | 10 mM |
| Purified water | 1 L |

The above components were mixed and pH was adjusted to 7.25 with NaOH. The osmotic pressure and electric conductivity of the first reagent were 20 mOsm/kg and 0.78 mS/cm, respectively.

The blood sample from the healthy donor was analyzed as described in Example 1 except that the above first reagent was used instead of the first reagent used in Example 1.

FIGS. 3 (1) to (4) show the obtained scattergrams.

As can be seen from FIGS. 3 (1) to (4), no signal is detected in the scattergram at a region where the potential signal of myeloblasts appears, because no myeloblast is contained in the blood sample from the healthy donor. No signal for lysed erythrocytes is appeared. Further, basophils do not appear in the myeloblast region because they are stained as intense as other mature leukocytes.

The ratio of myeloblasts to total leukocytes (ratio of myeloblasts=the number of myeloblasts/the number of total leukocytes×100) was 0%. The visually confirmed ratio of myeloblasts was also 0%.

Example 3

The analysis was performed as described in Example 1 except that instead of the blood sample from the healthy donor, a blood sample containing myeloblasts from a patient with acute myeloid leukemia was used, and side scattered light intensity, forward scattered light intensity and fluorescence intensity were analyzed.

FIGS. 4 (1) to (4) show the obtained scattergrams.

Based on the scattergrams of FIGS. 4 (1) to (4), the ratio of myeloblasts to total leukocytes was 1.2%. The visually confirmed ratio of myeloblasts of the same blood sample was 4.0%.

Examples 4 to 9

A first reagent and second reagent having the following composition were prepared.

FIGS. 5 to 11 show the obtained scattergrams. In respective figure of FIGS. 5 to 11, (A) shows a scattergram when the myeloblast sample was used as the blood sample and (B) shows a scattergram when the improper hemolysis sample was used as the blood sample. Normally, myeloblasts are detected in "BL" region in scattergrams.

The x-axis and y-axis of scattergrams of FIGS. 5 to 11 show the side scattered light intensity and fluorescence intensity, respectively. "Ly", "Mo", "Gran" and "IG" represent the sections in which lymphocytes, monocytes, granulocytes and immature granulocytes appear, respectively.

Based on these scattergrams, the ratios of myeloblasts to total leukocytes were calculated and described as "BL region" in FIGS. 6 to 11.

The results of FIGS. 5 to 11 show that when the analyses were carried out by using the reagent(s) of the present invention, myeloblasts were detected from the myeloblast sample and the ratio of myeloblasts was very low from the improper hemolysis sample. In addition, erythrocyte ghost, which is detected when the conventional reagent is used, was hardly detected in the analysis of the improper hemolysis sample. Therefore, it is shown that by using the present reagent(s), accurate analysis results can be obtained because myeloblasts are not incorrectly detected even when improper hemolysis samples were analyzed. Moreover, the myeloblast region and erythrocyte ghost region did not overlap on the scattergram when erythrocyte ghosts were detected (data not shown). Namely, it is shown that by using the present reagent(s), myeloblasts can be clearly distinguished from erythrocyte ghosts and immature leukocytes can accurately be measured even from blood samples such as those from multiple myeloma patients, because erythrocyte ghosts do not appear in the region of myeloblasts on scattergrams.

TABLE 1

| | | Examples (FIGS.) | | | | | | |
|---|---|---|---|---|---|---|---|---|
| | | 4 (FIG. 5) | 5 (FIG. 6) | 6 (FIG. 7) | 7 (FIG. 8) | 8 (FIG. 9) | 9 (FIG. 10) | 10 (FIG. 11) |
| First reagent | | | | | | | | |
| Surfactants (ppm) | Polyoxyethylene(15) oleyl ether | | | | | 2000 | 4000 | |
| | Polyoxyethylene(20) oleyl ether | 2500 | 5000 | 10000 | 20000 | 8000 | 16000 | 2500 |
| Solubilizing agent (ppm) | Sodium N-lauroylsarcosinate | 125 | 250 | 325 | 250 | 375 | 375 | 125 |
| Buffering agent (mM) | HEPES | | 30 | 30 | 30 | 30 | 30 | |
| | BES | 10 | | | | | | |
| | MOPSO | | | | | | | 10 |
| Medium | Purified water | 1 L | 1 L | 1 L | 1 L | 1 L | 1 L | 1 L |
| pH | | 7.0 | 6.75 | 6.75 | 6.65 | 7.25 | 7.25 | 7.0 |
| Osmotic pressure(mOsm/kg) | | 50 | 50 | 50 | 50 | 50 | 50 | 50 |
| Second reagent | | | | | | | | |
| Dye(ppm) | Dye A | 50 | 50 | 50 | 50 | 50 | 50 | 50 |
| Medium | Ethylene glycol | 1 L | 1 L | 1 L | 1 L | 1 L | 1 L | 1 L |

The first reagent (980 μL), 20 μL of the second reagent and 20 μl of any of the following blood samples were mixed and reacted at 35° C. for 13 seconds (17.5 seconds for Examples 4 and 11) to prepare measurement samples. Scattergrams were obtained as described in Examples 1 to 3.

As the blood sample, a blood sample from a leukemia patient containing myeloblasts (hereinafter referred to as "myeloblast sample") or a blood sample from a multiple myeloma patient containing no myeloblast (erythrocytes were lysed improperly) (hereinafter referred to as "improper hemolysis sample") was used.

The invention claimed is:

1. A reagent for analysis of immature leukocytes comprising:

a polyoxyethylene nonionic surfactant which can damage cell membranes of
erythrocytes and mature leukocytes, having the following formula (I):

wherein $R^1$ represents a $C_{9-25}$ alkyl, alkenyl or alkynyl group, $R^2$ represents —O—, —COO— or and n is an integer of 10 to 40,
a solubilizing agent which can shrink the damaged blood cells and
a dye for staining nucleic acid,
wherein the reagent has an osmotic pressure of not lower than 10 mOsm/kg and lower than 150 mOsm/kg and the pH of the reagent is from greater than 5.0 up to 9.0.

2. The reagent according to claim 1, wherein the concentration of the surfactant in the reagent is 500 to 15,000 ppm.

3. The reagent according to claim 1, wherein the polyoxyethylene nonionic surfactant is polyoxyethylene oleyl ether.

4. The reagent according to claim 3, wherein the polyoxyethylene oleyl ether has the formula (I) wherein n is 15 to 20.

5. The reagent according to claim 1, wherein the solubilizing agent is selected from the group consisting of a sarcosine derivative, a cholic acid derivative and methylglucanamide.

6. The reagent according to claim 1, wherein the concentration of the solubilizing agent in the reagent is 100 to 400 ppm when the solubilizing agent is a sarcosine derivative; 50 to 1,300 ppm when the solubilizing agent is a cholic acid derivative; and 500 to 1,100 ppm when the solubilizing agent is methylglucanamide.

7. The reagent according to claim 1, wherein the dye for staining nucleic acid is at least one dye selected from the group consisting of:

(1) a dye having the following formula (II):

(II)

wherein $R_1$ and $R_2$ are a lower alkyl group; n is 1 or 2; $X^-$ is an anion; and Z is a sulfur atom, an oxygen atom, or a carbon atom which is substituted by a lower alkyl group;

(2) a dye having the following formula (III):

(III)

wherein $R_1$ and $R_2$ are a lower alkyl group; n is 1 or 2; and $X^-$ is an anion:

3) a dye having the following formula (IV):

(IV)

wherein $R_1$ is a hydrogen atom or a lower alkyl group; $R_2$ and $R_3$ are a hydrogen atom, a lower alkyl group or a lower alkoxy group; $R_4$ is a hydrogen atom, an acyl group or a lower alkyl group; $R_5$ is a hydrogen atom or an optionally substituted lower alkyl group; Z is a sulfur atom, an oxygen atom, or a carbon atom which is substituted by a lower alkyl group; n is 1 or 2; and $X^-$ is an anion;

(4) a dye having the following formula (V):

(V)

wherein $X_1$ and $X_2$ are independently Cl or I;

(5) a dye having the following formula (VI):

(VI)

(6) a dye having the following formula (VII):

(VII)

(7) a dye having the following formula (VIII):

(VIII)

(8) a dye having the following formula (IX):

(IX)

(9) a dye having the following formula (X):

(10) propidium iodide or ethidium bromide;
(11) ethidium-acridine heterodimer, ethidium diazide, ethidium homodimer-1, ethidium homodimer-2, ethidium monoazide, trimethylene bis[[3-[[4-[[(3-methylbenzothiazol-3-ium)-2-yl]methylene]-1,4-dihydroquinoline]-1-yl]propyl]dimethylaminium]tetraiodide (TOTO-1), 4-[(3-methylbenzothiazol-2(3H)-ylidene)methyl]-1-[3-(trimethylaminio)propyl]quinolinium diiodide (TO-PRO-1), N,N,N',N'-tetramethyl-N,N'-bis[3-[4-[3-[(3-methylbenzothiazol-3-ium)-2-yl]-2-propenylidene]-1,4-dihydroquinoline-1-yl]propyl]1,3-propanediaminium tetraiodide (TOTO-3), or 2-[3-[[1-[3-(trimethyaminio)propyl]-1,4-dihydroquinoline]-4-ylidene]-1-propenyl]3-methylbenzothiazol-3-ium diiodide (TO-PRO-3).

8. A reagent kit for analysis of immature leukocytes comprising:
    a first reagent which comprises a polyoxyethylene nonionic surfactant that can damage cell membranes of erythrocytes and mature leukocytes, having the following formula (I):

wherein $R^1$ represents a $C_{9-25}$ alkyl, alkenyl or alkynyl group, $R^2$ represents —O—, —COO— or and n is an integer of 10 to 40,
    a solubilizing agent that can shrink the damaged blood cells wherein the first reagent has an osmotic pressure of not lower than 10 mOsm/kg and lower than 150 mOsm/kg and the pH of the first reagent is from greater than 5.0 up to 9.0, and
    a second reagent which comprises a dye for staining nucleic acid.

9. A method for classifying leukocytes comprising the steps of:
    mixing a biological sample possibly containing immature leukocytes with a reagent for analysis of immature leukocytes comprising a surfactant which can damage cell membranes of erythrocytes and mature leukocytes, having the following formula (I):

wherein $R^1$ represents a $C_{9-25}$ alkyl, alkenyl or alkynyl group, $R^2$ represents —O—, —COO— or and n is an integer of 10 to 40,
    a solubilizing agent which can shrink the damaged blood cells and a dye for staining nucleic acid, wherein the reagent has an osmotic pressure of not lower than 10 mOsm/kg and lower than 150 mOsm/kg and the pH of the reagent is from greater than 5.0 up to 9.0, to stain nucleic acid of mature leukocytes, and
    measuring at least one scattered light and at least one fluorescence of the immature leukocytes treated in the previous step to classify immature leukocytes based on differences of intensities of the scattered light and the fluorescence.

* * * * *